United States Patent
Raffalt

(10) Patent No.: US 7,146,845 B2
(45) Date of Patent: Dec. 12, 2006

(54) METHOD FOR OPERATING TESTS OF VIBRATION LEVEL SWITCH SENSORS AND CORRESPONDING VIBRATION LEVEL SWITCH

(75) Inventor: Felix Raffalt, Hausach (DE)

(73) Assignee: Vega Grieshaber KG, Wolfach (DE)

( * ) Notice: Subject to any disclaimer, the term of this patent is extended or adjusted under 35 U.S.C. 154(b) by 193 days.

(21) Appl. No.: 10/808,003

(22) Filed: Mar. 24, 2004

(65) Prior Publication Data

US 2005/0210954 A1 Sep. 29, 2005

(51) Int. Cl.
*G01F 1/00* (2006.01)
(52) U.S. Cl. ............... 73/1.83; 73/1.73
(58) Field of Classification Search ........ 73/1.73, 73/1.83, 1.82, 1.85, 149, 290 V
See application file for complete search history.

(56) References Cited

U.S. PATENT DOCUMENTS

| | | | | |
|---|---|---|---|---|
| 4,299,114 A | * | 11/1981 | Silvermetz et al. | ......... 73/1.83 |
| 5,261,274 A | * | 11/1993 | Nemirow | ............... 73/149 |
| 5,743,134 A | | 4/1998 | Dreyer | |
| 5,895,848 A | * | 4/1999 | Wilson et al. | ........... 73/290 V |
| 2002/0057094 A1 | | 5/2002 | Raffalt et al. | |

FOREIGN PATENT DOCUMENTS

| | | |
|---|---|---|
| DE | 42 32 719 | 3/1994 |
| DE | 198 35 370 | 2/2000 |
| DE | 198 40 796 | 9/2000 |
| DE | 100 56 353 | 5/2002 |
| EP | 0 853 236 | 7/1998 |

* cited by examiner

*Primary Examiner*—Robert Raevis
(74) *Attorney, Agent, or Firm*—Fay Kaplun & Marcin, LLP

(57) ABSTRACT

A method for carrying out operating tests of vibration level switches for liquids or solid bulk material or mixtures thereof is provided, whereby a vibration resonator (1) of a level detection sensor is excited by an oscillation exciting feedback circuit to oscillate, whereby at least one excitation parameter of a plurality of signal processing blocks (5, 6, 7, 8, 9, 10) of the feedback circuit is varied, and the resulting oscillation change is compared by a microprocessor (14) to datasets comprising data of corresponding oscillation changes of a failure free system. Moreover, a vibration level switch for measuring the level in containers for carrying out the inventive method is provided.

22 Claims, 2 Drawing Sheets

METHOD FOR OPERATING TESTS OF VIBRATION LEVEL SWITCH SENSORS AND CORRESPONDING VIBRATION LEVEL SWITCH

TECHNICAL FIELD OF THE INVENTION

The present invention relates to a method for an operating test of vibration level switches as well as to a vibration level switch, adapted to carry out the operating test.

The invention is applicable to vibration level switches which are employed for measuring solid bulk material as well as vibration level switches which are employed for measuring liquids in containers.

BACKGROUND OF THE INVENTION

Vibration level switch systems usually consist of a vibration resonator and an oscillation exiting feedback circuit coupled thereto which during operation of the system excites the vibration resonator to its resonance frequency such that a self-preserving oscillation results.

In prior art, vibration sensors may be known, operating on this principle. For testing the faultless functioning of such a sensor system, instead of the vibration sensor, a band pass filter is connected to the feedback circuit. The generated oscillation frequency, determined by the band pass filter, is stored during an initialization calibration and is compared to reference frequency values obtained during subsequent test measurements.

However, this method for testing the functioning is only suitable for liquid level switch sensors analyzing the frequency. The electronic of the feedback circuit and the subsequent stages are tested for failures by means of this method. A testing of the sensor mechanism is not possible.

Another method for testing the operation of a vibration sensor for level detection of solid bulk material is to set the amplification factor of the feedback circuit to a fixed low value such that with the sensor not covered by bulk material, a signal is output, indicating a full container, or is set to a fixed height value, such that with the sensor covered completely, a signal is output, indicating that the container is empty.

The process is suitable for solid bulk material level switch sensors analyzing the amplitude. However, only very rough changes of the sensor can be detected by this method.

In prior art, another vibration sensor is known, being also excited by means of a feedback circuit to its resonant frequency. For compensating manufacturing tolerances, the switching parameters of the feedback circuit can be changed on the basis of a characteristic element which is assigned to the sensor mechanism. However, with this sensor, no operating tests are possible at all.

Therefore, there would be a need for a method, according to which liquid as well as solid bulk material vibration sensors can be tested for their correct functioning. It would also be meaningful that by means of the operating test, also the oscillation exciting feedback circuit is tested as well as the subsequent signal processing stages, as well as the connection lines to the respective electronics, the electromechanical converter system and finally also the mechanical system of the sensor.

Moreover, it would be meaningful to not only detect failures leading to the complete failure of the vibration sensor but also failures which only result in a change of the measurement properties without leading to complete failure of the sensor system.

SUMMARY OF THE INVENTION

Implementations of the invention can include one or more of the following features.

According to an aspect of the invention, a method for carrying out operating tests of vibration level switches for liquids or solid bulk material, whereby a level detection sensor is excited by an oscillation exciting feedback circuit to oscillate, whereby at least one excitation parameter of a plurality of signal processing blocks of the feedback circuit is varied, and the resulting oscillation change is compared by a microprocessor to datasets comprising data of corresponding oscillation changes of a failure free system.

Thus, according to the inventive operating test method, the same mechanical, electrical, and electronic sensor components can be used for normal level detection operation as are used in the operating tests itself. Moreover, the entire signal chain can be incorporated into the test. The sensor is measured in the range of its operational resonance point and is thus very realistic, also with respect to surrounding vibrations and electromagnetic scattering. Due to the high signal amplitude available, it is also relatively failure-resistant. This is a great advantage with respect to operating test methods, exciting the sensor outside its operating resonance range. Due to the very small oscillation amplitudes, which are obtainable thereby, external vibrations and electromagnetic scattering could simulate totally changed sensor characteristics.

Another aspect of the invention is to be able to detect any operational fault of the whole vibration level switch system by means of the deviation of the amplitude and frequency change resulting from the variation of a distinct excitation parameter from a reference dataset stored in a memory, comprising changes of amplitude and frequency due to the variation of a distinct excitation parameter of a failure free system.

According to a further aspect of the invention, the variation of the excitation parameters is carried out via control lines, connecting the respective signal processing blocks to the microprocessor. A self-preserving oscillation of the vibration resonator is generated by the following steps: supplying a first output signal of a detection crystal comprised in the vibration resonator to the signal processing blocks of the oscillation feedback circuit, whereby a second output signal is generated from the first output signal after passing through the oscillation feedback circuit, which in turn is supplied to an excitation crystal comprised in the vibration resonator.

According to another aspect of the invention the type of the excitation parameter variation and the evaluation of its effect are carried out in dependency of the oscillation amplitude and frequency of the vibration resonator detected prior to carrying out the operating test.

Moreover, according to a further aspect of the invention the change of excitation parameters for identifying deviations based on a malfunction is determined empirically, whereby the change of the excitation parameters and the corresponding deviations are stored in the memory.

Another aspect of the invention is that in the memory is stored: data for an initial pair of variates, consisting of amplitude and frequency and corresponding amplitude and frequency values of the system with a faultless sensor or faultless components, as well as a corresponding allowance band for a sensor function, which is not sound but still acceptable.

For each initial pair of variates, several operating test datasets are stored. Several excitation parameters settings are carried out sequentially for a complete operating test of the sensor.

The initial pair of variates for carrying out the operating test is formed by the actual amplitude and frequency of the sensor, according to which the corresponding test dataset is selected from the memory, on the basis of which the microprocessor changes the excitation parameters of at least one of the signal processing blocks via the control lines.

According to another aspect of the present invention, a notice of malfunction is output, if during the operating test, a first allowance band of the data set is exceeded. A warning signal is output after the operating test, if critical values are reached within a second allowance band which is narrower than the first allowance band.

In another aspect of the invention it is provided for the operating test to be carried out automated cyclically. Another possibility is that the operating test is initiated by external input of a test command. An advantage is that the same signal processing blocks, which are used for the carrying out of the operating test, are also used for measuring the level in a container.

According to a further aspect of the present invention, data of the oscillation change of faultless systems is stored in a non-volatile semiconductor memory. Moreover, the operating test is carried out for the sensor mechanism as well as for the electronics of the feedback circuit and its subsequent stages.

Yet another aspect of the invention is that the sensor of the level switch is excited to oscillations by an oscillation exciting feedback circuit, whereby at least one excitation parameter of a plurality of signal processing blocks forming the feedback circuit is varied to carry out the test, whereby the response values of amplitude and frequency of the level switch sensor are compared to pair of values stored in a memory after changing the excitation parameters corresponding to a faultless operation of the system, whereby due to exceeding of a first allowance band, also stored in the memory, the notice of malfunction is output via a line, or a warning signal is output, respectively, due to reaching critical values within a second allowance band, being narrower than the first allowance band, stored in the memory.

According to still another aspect of the invention, a vibration level switch for measuring the level in containers is provided, comprising a vibration resonator, which is adapted to output a first output signal, generated by an oscillation detector crystal contained in the vibration resonator, to a plurality of signal processing blocks constituting an oscillation exciting feedback circuit, which are adapted to process the first output signal and output a second output signal to an excitation crystal contained in the vibration resonator, to effect a self-preserving oscillation of the vibration resonator on its resonance frequency, whereby the signal processing blocks are connected to a microprocessor via control lines, whereby the microprocessor is adapted to read and select test datasets from a memory for carrying out the operating test by changing the excitation parameters via the control lines.

The memory is for example adapted for storing values of the excitation parameters to be changed during the operating test. The memory can further be adapted to store pair of variates, consisting of amplitude and frequency, corresponding to a faultless operation of the components of the vibration level switch system.

Yet another aspect of the present invention is that the memory is adapted to contain test datasets with scheduled values, corresponding to faultless operation of the components of the vibration level switch system.

Further, the memory is adapted to store first allowance bands for each pair of variates, whereby the microprocessor is adapted to output a notice of malfunction over a line, when the first tolerance band is exceeded according to a further aspect of the invention. The memory for example is also adapted to store second allowance bands for each pair of variates, being narrower than the first allowance bands, whereby the microprocessor is adapted to output a warning signal over the lines, when critical values within the second allowance bands are reached.

According to still another aspect of the present invention, a vibration level switch is provided, whereby the plurality of signal processing blocks comprises at least one of the components of the group consisting of: receive amplifier, high pass filter, low pass filter, phase shift stage, maximum value restriction stage, drive stage, band pass filter, band elimination filter, signal blanking means, level logarithmizer.

Finally, it is an aspect of the present invention that the signal processing blocks are adapted to be excitation parameter controllable.

BRIEF DESCRIPTION OF THE DRAWINGS

Exemplary embodiments of the invention will now be described by way of example with reference to the accompanying drawing, in which.

DETAILED DESCRIPTION OF AN EXEMPLARY EMBODIMENT OF THE PRESENT INVENTION

Figure 1:
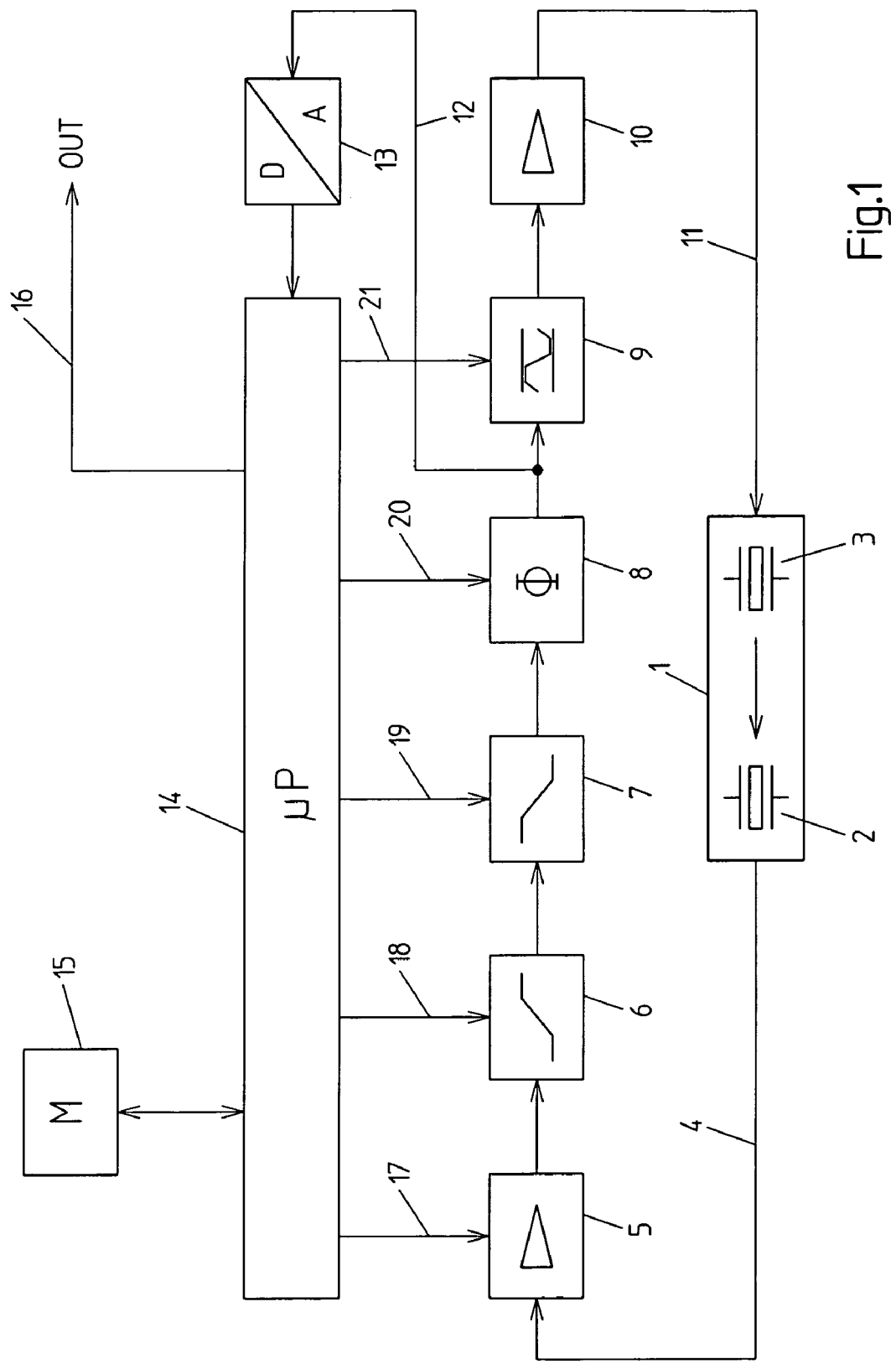
FIG. 1 is a schematic diagram of a vibration level switch system according to the invention.

FIG. 1 shows a schematic diagram of the inventive vibration level switch system. First, the normal functioning for a measurement of the inventive sensor arrangement is described without an operating test being carried out.

Vibration resonator 1, being realized as a tuning fork, is dipped into the liquid or solid bulk material to be measured. For excitation and detection of mechanical oscillations, resonator 1 is equipped with an electromechanical converter system, comprising a piezo-electric oscillation detection crystal 2 and an oscillation excitation crystal 3. The electrical output signal 4 of detection crystal 2 is supplied to blocks 5 to 10, forming an oscillation exciting feedback circuit. A second output signal, which is the processed first output signal, namely output signal 11, serves for controlling excitation crystal 3. By means of the signal filter and amplification effect of the feedback circuit, a self-preserving oscillation of the vibration resonator 1 on its resonance frequency is enabled.

Now, the operation of the feedback circuit, comprising signal processing blocks 5 to 10 is explained in the following. The oscillation detection signal 4 is supplied to a receive amplifier 5, amplifying it to a voltage level adequate for the subsequent further signal processing. The high pass filter 6, following the receive amplifier 5, suppresses signal components being below the basic oscillation resonance frequency of the resonator 1. The next component connected in line to high pass filter 6 is a low pass filter 7, suppressing frequency portions above the desired basic oscillation frequency. Filters 6 and 7 define the transmission frequency range of the feedback circuit. The phase shift stage 8 following low pass filter 7 serves for adapting the total phase shift of the feedback circuit between signals 4 and 11, to a value suitable for oscillation excitation of the vibration resonator 1.

The subsequent maximum value restriction stage 9 stabilizes the oscillation amplitude of the system to a defined maximum value, in that a further signal rise is prevented, starting at a certain control voltage level, by cutting off the positive and negative voltage level half-wave. The subsequent drive stage 10 serves for direct control of the oscillation excitation piezo-crystal 3. Besides its amplifier function, it can also comprise measures for restricting the signal rise velocity, to remove harmonic components of the excitation signal generated by the maximum value restriction stage 9. The analysis of the vibration resonator oscillation is carried out by a microprocessor 14. An intermediate signal 12, lying between the signal processing blocks 8 and 9, is supplied to microprocessor 14 after digitalization by means of an analogue digital converter 13.

Microprocessor 14 determines amplitude and frequency of the oscillation, compares them to predetermined threshold values, and from these, determines the covering state of the vibration resonator 1. The result is transferred via line 16 to an output or interface unit (not shown).

Now, also the inventive operating test method is explained. First, adequate test parameters for a given vibration sensor type are determined. During normal level detection measurement, the excitation parameters of the feedback circuit 5 to 10 are selected such that the variable bulk material or liquid cover, to be detected by the vibration resonator, are converted into characteristic signal amplitude or frequency values, respectively, which can be easily analyzed.

For generating additional measurement values, providing indirect information concerning the sensor properties and thus concerning the functionality of the sensor system, microprocessor 14 is equipped with control lines 17 to 21, enabling the changing of the excitation parameters of the feedback circuit 5 to 10.

In the illustrated example, blocks 5 to 9 can be controlled with respect to their signal processing properties by microprocessor 14. Thus, the receive amplifier 5, the high and low pass filters 6 and 7, the phase shift stage 8, and the maximum value restriction stage 9 can be adjusted. The change of the signal processing properties of one or several blocks results in that the vibration resonator reacts with a changed oscillation amplitude and frequency. The magnitude of the change of values, thereby, is not only directly dependent on the parameter variation carried out on the signal processing block, but rather also on the other signal processing properties of the feedback circuit as well as the physical construction of the vibration resonator.

Additionally, the change of value is dependent on the solid or liquid bulk material, presently coupled to the resonator and their damping properties. The influence of the bulk material is taken into account in such a manner that the type of the excitation parameter variation and the evaluation of its effect is carried out dependently of the oscillation amplitude and frequency of the vibration resonator measured prior to carrying out of the operating tests.

In a plurality of tests it is determined, which change of excitation parameters is especially favorable, to convert simulated failures or defects in the sensor mechanism and electronics at a given resonator amplitude and frequency into particularly characteristic deviations to a failure-free sensor with respect to the obtained amplitude and frequency response value of the oscillation system.

In a further step, datasets for carrying out an operating test are provided. For each initial pair of variates, consisting of amplitude and frequency, the values of the excitation parameters to be changed deviating from normal sensor operation are stored. Additionally, amplitude and frequency response values of the system, including an associated allowance band for still acceptable sensor function are stored of a failure-free sensor. In order to completely test the sensor, usually different excitation parameter settings have to be carried out subsequently such that for each initial pair of variates, several functional test datasets are to be stored.

The storing results in a nonvolatile semiconductor memory 15, accessible by the microprocessor 14.

For reducing the initial pair of variates, for which datasets exist, a sufficient distance is selected between these, and a calculation procedure is stored in microprocessor 14, how to calculate testing data for intermediate values lying in between by means of interpolation. To not measure every single manufactured sensor completely during sensor production, reference datasets of sensors are generated having particularly high and low basic frequencies and oscillation amplitudes, respectively. For a single sensor produced, simply the amplitude and frequency are measured in an uncovered state as well as in a state covered with reference bulk material, and test datasets are calculated on the basis of these values from the reference datasets.

The operating test can be carried out automated cyclically or by external input of a test command. When an operating test is carried out, the actual oscillation amplitude and frequency of the level switch sensor form the initial pair of variates for the microprocessor 14, by means of which it chooses the first test dataset from memory 15 after interpolation calculation possibly required. The microprocessor 14 now changes the signal processing parameters of signal processing blocks 5 to 9 by means of control lines 17 to 21, according to the data read. The sensor system now is operated with the changed excitation parameters, and responds with new amplitude and frequency values.

Microprocessor 14 checks, whether the two values are lying within the admissible allowance band of the dataset stored, and, when exceeding the allowance band, outputs a malfunction signal via line 16.

In case, the allowance band was met, the next test dataset stored with respect to the initial pair of variates is read out from memory 15, and the sensor is tested with the further excitation parameter setting. After applying all test data sets, the sensor system returns to normal level detection measurement operation, as long as no failure was detected.

However, if besides the output of a malfunction signal indicating only a sensor which has already failed, additionally a warning signal is desired, indicating that the measurement property of the sensor is deteriorating, this can be realized in that two different allowance bands are stored being of different width. In case that as a test result the narrower allowance band is exceeded, but the wider one has been met, only a warning signal can be output.

Besides the parameter variable signal processing blocks 5 to 9, shown in FIG. 1, also other stages as band pass filters, band elimination filters, signal blanking means or level logarithmizers can be employed in the feedback circuit and can be parameter controllable for test purposes.

In the case of vibration level switch sensors, according to which the oscillation can stop during normal operation (solid bulk material sensor with material covering), in this state the amplification setting of block 5 is raised during the operating test so far that still an oscillation is initiated in the resonator, and the occurring signal amplitude and frequency can be compared to the desired values stored in memory 15.

The effect of the excitation parameter change is shown in the following by way of two particular failure conditions: an oscillation, bypassing the resonator is generated by an internal electrical or mechanical overcoupling failure. In this case, the oscillation frequency can be changed by variation of filters 6 and 7 over an abnormal wide range, without that the oscillation ceases. The oscillation reacts, however, very sensitive to changes of phase shift stage 8.

Another example is that a pretended useful signal is generated by strong vibrations of the surroundings or electromagnetic scattering. In this case, the oscillation frequency cannot be changed in its value by variation of filters 6 and 7, but rather can only influence the signal amplitude. A change of phase shift stage 8 has no influence on the oscillation. Without the employment of the operating test method in both cases an arbitrary level value would be pretended. By variation of the excitation parameters, it is possible by means of the inventive method, to detect the different characteristic of the signal, and thus to detect a sensor failure by means of comparison to the behavior of a failure-free sensor system.

Figure 2:
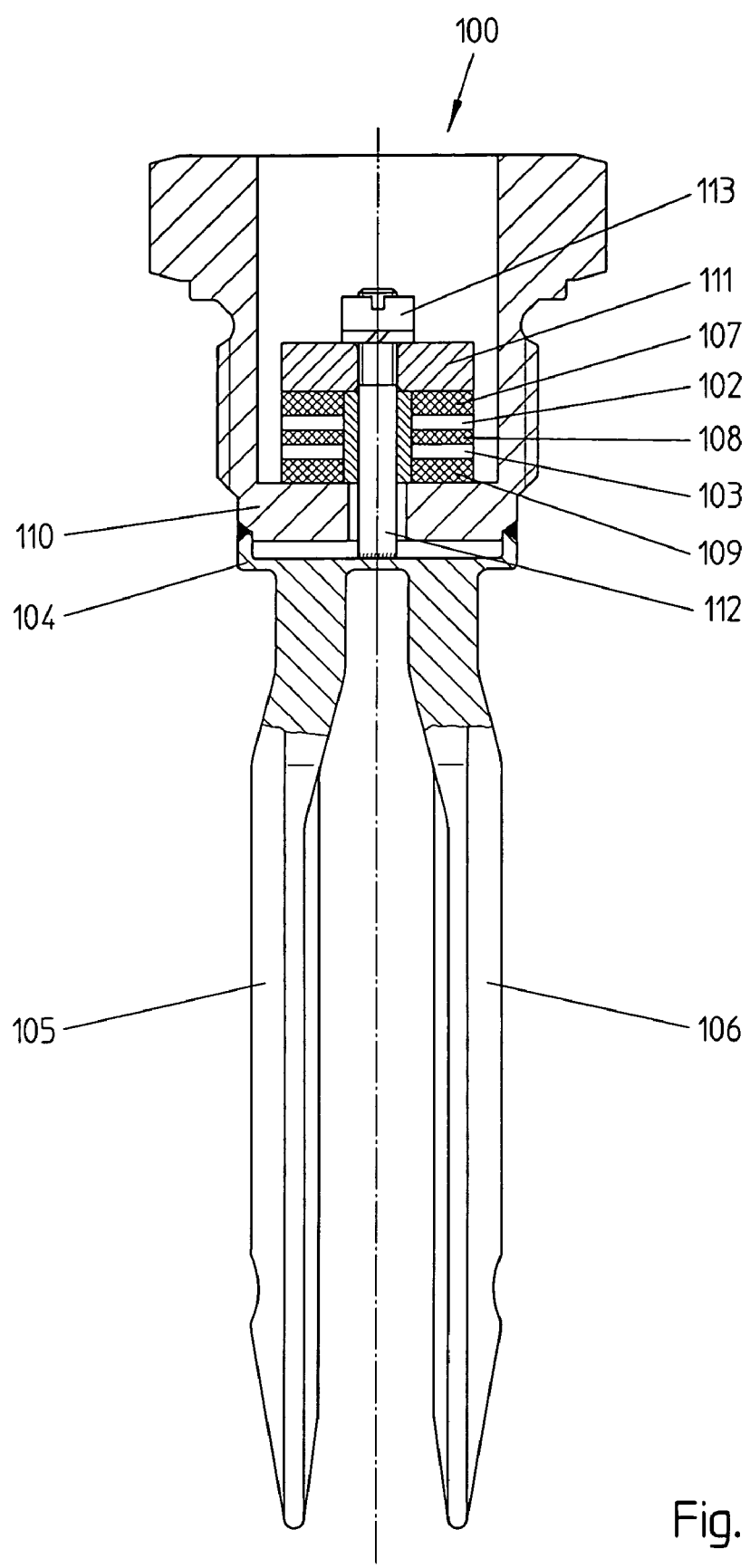
FIG. 2 is a schematic side view of a vibration level sensor element according to the invention.

An exemplary embodiment of a vibration level sensor element 100 according to the invention is shown in FIG. 2.

FIG. 2 shows a tuning fork resonator with an integrated electromechanical transducer system. The tuning fork resonator comprises two fork prongs 105, 106 and a membrane 104. The electromechanical transducer system comprises a vibration detecting crystal 102, a vibration exciting crystal 103 and isolating ceramic discs 107, 108, 109. The vibration coupling of the mechanical resonator and the transducer system is carried out by a bottom plate 110, a pressure disc 111 and a tension bolt 112. The whole assembly is mechanically pre-stressed by a screw element 113. As the fork prongs 105, 106 immerse into a filling material to be measured, the amplitude and the oscillation frequency of the fork prongs 105, 106 vary.

The invention claimed is:

1. A method for carrying out an operating test of a vibration level switch for liquids or solid bulk material or mixtures thereof, whereby a vibration resonator of a vibration level switch system is excited by an oscillation exciting feedback circuit to oscillate, whereby at least one excitation parameter of a plurality of signal processing blocks of the feedback circuit is varied, and the resulting oscillation change is compared by a data processing unit to datasets comprising data of corresponding oscillation changes of a failure free system, wherein any operational fault of the vibration level switch is determined by the deviation of the amplitude and frequency change resulting from the variation of a distinct excitation parameter from a reference data set stored in a memory, comprising changes of amplitude and frequency due to the variation of a distinct excitation parameter of a failure free system.

2. The method according to claim 1, whereby the variation of the excitation parameters is carried out via control lines, connecting the respective signal processing blocks to a microprocessor.

3. The method according to claim 1, wherein a self-preserving oscillation of the vibration resonator is generated by the following steps:

supplying a first output signal of a detection crystal comprised in the vibration resonator to the signal processing blocks of the oscillation feedback circuit, whereby a second output signal is generated from the first output signal after passing through the oscillation feedback circuit, which in turn is supplied to an excitation crystal comprised in the vibration resonator.

4. The method according to claim 1, whereby the type of excitation parameter variation and the evaluation of its effect is carried out in dependency of the oscillation amplitude and frequency of the vibration resonator detected prior to carrying out the operating test.

5. The method according to claim 1, whereby the change of excitation parameters for identifying deviations based on a malfunction are determined empirically, whereby the change of excitation parameters and the corresponding deviations are stored in the memory.

6. The method according to claim 1, whereby in the memory is stored:

data for an initial pair of variates, consisting of amplitude and frequency and corresponding amplitude and frequency values of the system with a faultless sensor or faultless components, as well as a corresponding allowance band for a sensor function, which is not sound but still acceptable.

7. The method according to claim 6, whereby for each initial pair of variates, several operating test datasets are stored.

8. The method according to claim 1, whereby several excitation parameters settings are carried out sequentially for a complete operating test of the sensor.

9. The method according to claim 1, whereby the initial pair of variates for carrying out the operating test is formed by the actual amplitude and frequency of the sensor, according to which the corresponding test dataset is selected from a memory, on the basis of which a microprocessor changes the excitation parameters of at least one of the signal processing blocks via control lines.

10. The method according to claim 1, whereby a notice of malfunction is output, if during the operating test, a first allowance band of the data set is exceeded.

11. The method according to claim 10, whereby a warning signal is output after the operating test, if critical values are reached within a second allowance band which is narrower than the first allowance band.

12. The method according to claim 1, whereby the operating test is carried out automated cyclically.

13. The method according to claim 1, whereby the operating test is initiated by external input of a test command.

14. The method according to claim 1, whereby the same signal processing blocks, which are used for the carrying out of the operating test, are also used for measuring the level in a container.

15. The method according to claim 1, whereby data of the oscillation change of faultless systems are stored in a non-volatile semiconductor memory.

16. A method for carrying out an operating test of a vibration level switch for liquids or solid bulk material or mixtures thereof, whereby, a vibration resonator of the vibration level switch is excited to oscillations by an oscillation exciting feedback circuit, whereby at least one excitation parameter of a plurality of signal processing blocks forming the feedback circuit is varied to carry out the test, whereby the response values of amplitude and frequency of the level switch sensor are compared to a pair of values stored in a memory after changing the excitation parameters corresponding to a faultless operation of the system, whereby due to exceeding of a first allowance band, also stored in the memory, the notice of malfunction is output via a line, or a warning signal is output, respectively, due to reaching critical values within a second allowance band, being narrower than the first allowance band, stored in the memory.

17. A vibration level switch for carrying out an operating test to measure solid bulk and liquid levels in a container, comprising a vibration resonator, which is adapted to output a first output signal, generated by an oscillation detector crystal contained in the vibration resonator, to a plurality of signal processing blocks constituting an oscillation exciting feedback circuit, which are adapted to process the first output signal and output a second output signal to an excitation crystal contained in the vibration resonator, to effect a self-preserving oscillation of the vibration resonator on its resonance frequency, whereby the signal processing blocks are connected to a microprocessor via control lines, whereby the microprocessor is adapted to read and select test datasets from a memory for carrying out the operating test by changing the excitation parameters via the control lines, whereby the memory is adapted to store a pair of variates comprising amplitude and frequency variates, said amplitude and frequency variates corresponding to a faultless operation of the components of the vibration level switch system.

18. The vibration level switch according to claim 17, whereby the memory is adapted for storing values of the excitation parameters to be changed during the operating test.

19. The vibration level switch according to claim 17, whereby the memory is adapted to contain test datasets with scheduled values, corresponding to faultless operation of the components of the vibration level switch system.

20. The vibration level switch according to claim 17, whereby the memory is adapted to store first allowance bands for each pair of variates, whereby the microprocessor is adapted to output a notice of malfunction over a line, when the first allowance band is exceeded.

21. The vibration level switch according to claim 20, whereby the memory is adapted to store second allowance bands for each pair of variates, being narrower than the first allowance bands, whereby the microprocessor is adapted to output a warning signal over the lines, when critical values within the second allowance bands are reached.

22. The vibration level switch according to claim 17, whereby the signal processing blocks are adapted to be excitation parameter controllable.

* * * * *